United States Patent
Zhou

(10) Patent No.: US 8,481,743 B2
(45) Date of Patent: Jul. 9, 2013

(54) PHENYLPROPIONAMIDE COMPOUNDS AND THE USE THEREOF

(75) Inventor: Xiaoming Zhou, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 469 days.

(21) Appl. No.: 12/447,758

(22) PCT Filed: Oct. 31, 2007

(86) PCT No.: PCT/IB2007/003411
§ 371 (c)(1),
(2), (4) Date: Apr. 2, 2010

(87) PCT Pub. No.: WO2008/053352
PCT Pub. Date: May 8, 2008

(65) Prior Publication Data
US 2010/0234426 A1 Sep. 16, 2010

Related U.S. Application Data

(60) Provisional application No. 60/855,826, filed on Nov. 1, 2006.

(51) Int. Cl.
*C07D 211/56* (2006.01)
*A61K 31/445* (2006.01)

(52) U.S. Cl.
USPC ............................ 546/223; 546/224; 514/329

(58) Field of Classification Search
USPC .................. 546/223, 224; 514/329
See application file for complete search history.

(56) References Cited

U.S. PATENT DOCUMENTS

| | | |
|---|---|---|
| 3,655,675 A | 4/1972 | Carabateas |
| 3,679,690 A | 7/1972 | Carabateas |
| 3,763,168 A | 10/1973 | Carabateas |

FOREIGN PATENT DOCUMENTS

| | | |
|---|---|---|
| WO | WO 97/43279 | 11/1997 |
| WO | 9944596 A1 | 9/1999 |
| WO | WO 99/51578 | 10/1999 |

OTHER PUBLICATIONS

Leonard et al Bio. Med Chem Letter 2006, 16, 4467-4474.*
Afantitis et al Journal of Computer-Aided Molecular Design 2006, 20, 83-95.*
Cumming et al Bio Med Chem Lett 2005, 15, 5012-5015.*
Burrows et al Bio. Med Chem Letter 2005, 15, 25-28.*
CAS Abstract Acc. No. 1994:323214, DN 120:323214. Yang et al. Synthesis and anesthetic activity of 3-methyl fentanyl derivatives. Zhongguo Yaoke Daxue Xuebao 24(5): 257-263 (1993).

* cited by examiner

*Primary Examiner* — Janet Andres
*Assistant Examiner* — John Mabry
(74) *Attorney, Agent, or Firm* — Purdue Pharma L.P.; Marian E. Fundytus; Alan L. Koller

(57) ABSTRACT

The invention relates to phenylpropionamide compounds of Formula (I): and pharmaceutically acceptable salts, prodrugs, and solvates thereof, wherein A, B, $R^1$, $R^2$, $R^3$, $R^4$ and $R^5$ are defined as set forth in the specification. The invention is also directed to the use of compounds of Formula (I) to treat, prevent or ameliorate a disorder responsive to the activation of opioid receptors, particularly μ-opioid receptors. Compounds of the present invention are especially useful for treating pain.

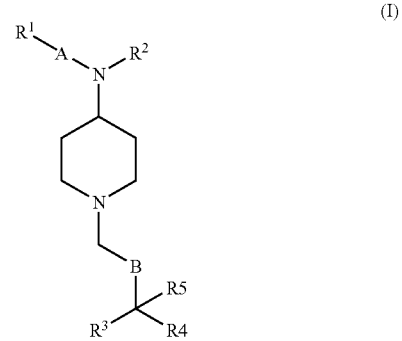

(I)

14 Claims, No Drawings

PHENYLPROPIONAMIDE COMPOUNDS AND THE USE THEREOF

This is the National Stage of PCT application number PCT/IB2007/003411, filed 31 Oct. 2007, which claims the benefit of U.S. provisional application Ser. No. 60/855,826, filed 1 Nov. 2006.

FIELD OF THE INVENTION

This invention is in the field of medicinal chemistry. The invention relates to novel phenylpropionamide compounds that act as opioid agonists.

BACKGROUND ART

Pain is the most common symptom for which patients seek medical advice and treatment. Pain can be acute or chronic. While acute pain is usually self-limited, chronic pain can persist for 3 months or longer and lead to significant changes in a patient's personality, lifestyle, functional ability or overall quality of life (K. M. Foley, Pain, in Cecil Textbook of Medicine 100-107, J. C. Bennett and F. Plum eds., 20$^{th}$ ed. 1996).

Pain has been traditionally managed by administering a non-opioid analgesic, including but not limited to acetylsalicyclic acid, choline magnesium trisalicylate, acetaminophen, ibuprofen, fenoprofen, diflusinal and naproxen; or an opioid analgesic, including but not limited to morphine, hydromorphone, methadone, levorphanol, fentanyl, oxycodone and oxymorphone. Id.

U.S. Pat. Nos. 6,576,650 6,166,039 and 5,849,761 to Yaksh, and U.S. Pat. No. 6,573,282, to Yaksh et al., describe 1,4-substituted piperidine derivatives for use as peripherally acting anti-hyperalgesic opiates.

U.S. Pat. No. 6,362,203 B1 to Mogi et al. describes 4-hydroxy-4-phenylpiperidine derivatives that have peripheral analgesic action.

Canadian Patent Publication No. 949560 of Carron et al. describes piperidine derivatives for use as analgesics.

International PCT Publication WO 02/38185 A2 by Dunn et al. describes 1,4-substituted piperidine compounds for use as anti-hyperalgesic opiates.

International PCT Publication WO 01/70689 A1 describes piperidine derivatives for use as opioid δ receptor agonists.

Traditional opioid analgesics exert their pharmacological activity once they have passed through the blood-brain barrier (BBB). But passage through the BBB can lead to undesirable central nervous system (CNS)-mediated side effects, such as respiratory depression, increased drug tolerance, increased drug dependence, constipation and unwanted euphoria.

There remains a continuing need for new drugs that can be used to treat or prevent pain, and that reduce or avoid one or more side effects associated with traditional therapy.

BRIEF SUMMARY OF THE INVENTION

The present invention is related to the use of phenylpropionamide compounds represented by Formula I, below, and the pharmaceutically acceptable salts, prodrugs and solvates thereof, as agonists of opioid receptors. Certain compounds of Formula I are expected to show selectivity for the μ opioid receptor. Certain compounds of Formula I are expected to not readily cross the BBB, and therefore to effectively remain in the periphery.

The present invention is also related to treating, preventing or ameliorating a disorder responsive to the activation of opioid receptors in a mammal suffering from such a disorder by administering an effective amount of a compound of Formula I, or a pharmaceutically acceptable salt, prodrug or solvate thereof, as described herein. More specifically, the invention is related to treating, preventing or ameliorating a disorder responsive to the activation of opioid receptors outside of the CNS (i.e., in the peripheral nervous system), in a mammal suffering from such a disorder, by administering an effective amount of a compound of Formula I, or a pharmaceutically acceptable salt, prodrug or solvate thereof, as described herein.

In one aspect the present invention is directed to treating, preventing or ameliorating a disorder responsive to the activation of opioid receptors in a mammal suffering from such a disorder by administering an effective amount of a compound of Formula I, or a pharmaceutically acceptable salt, prodrug or solvate thereof, as described herein. In particular preferred disorders which are treated, prevented or ameliorated by the activation of an opioid receptor are pain, such as chronic pain, neuropathic pain, inflammatory pain, pain due to osteoarthritis, pain due to rheumatoid arthritis, cancer pain, pain due to spinal cord injury, surgical pain or acute pain, diarrhea, neurological disorders such as Parkinson's disease, Huntington's chorea, Alzheimer's disease, anxiety, depression, stress disorders, memory loss e.g. due to Alzheimer's disease and/or dementias, or epilepsy. Furthermore, the compounds of the present invention may be used as anesthetic agents, neuroprotective agents, agents to treat neurological disorders such as Parkinson's disease, anxiolytic agents, anti-depressant agents, agents to treat stress disorders, agents to treat memory loss e.g. due to Alzheimer's disease and (or dementias, anti-epileptic or anti-convulsant agents.

In one aspect the present invention provides novel compounds of Formula I, and the pharmaceutically acceptable salts, prodrugs and solvates thereof.

In a further aspect, the present invention provides pharmaceutical compositions useful for treating, preventing or ameliorating a disorder responsive to the activation of opioid receptors, said pharmaceutical composition containing an effective amount of a compound of Formula I, or a pharmaceutically acceptable salt, prodrug or solvate thereof, optionally admixed with one or more pharmaceutically acceptable carriers or excipients.

In a further aspect, the present invention provides a method for treating, preventing or ameliorating pain (e.g. chronic pain, neuropathic pain, inflammatory pain, surgical pain or acute pain), or diarrhea, by administering an effective amount of a compound of Formula I, or a pharmaceutically acceptable salt, prodrug or solvate thereof, to a mammal in need of such treatment, prevention or amelioration.

In a further aspect, the present invention provides a method of modulating activity at an opioid receptor comprising exposing the receptor to an effective amount of at least one compound of Formula I, or a pharmaceutically acceptable salt, prodrug or solvate thereof.

In a further aspect, the present invention provides the use of a compound of Formula I, or a pharmaceutically acceptable salt, prodrug or solvate thereof, in the manufacture of a medicament for treating, preventing or ameliorating pain (e.g. chronic pain, neuropathic pain, inflammatory pain, surgical pain or acute pain) in a mammal, or for treating, preventing or ameliorating diarrhea in a mammal.

In a further aspect, the present invention provides radiolabeled compounds of Formula I and the use of such compounds, or their pharmaceutically acceptable salts, prodrugs or solvates, as radioligands for binding to an opioid receptor. Utilizing such radio-labeled (e.g., $^3$H, $^{11}$C or $^{14}$C-radio-labeled) compounds, the present invention further provides a method for screening a candidate compound for the ability to bind to an opioid receptor. This method comprises: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only, and are not restrictive of the invention, as claimed.

DETAILED DESCRIPTION OF THE INVENTION

The present invention provides compounds of Formula I as defined below, and the pharmaceutically acceptable salts, prodrugs and solvates thereof, which compounds are useful as opioid receptor agonists. Compounds of Formula I, and the pharmaceutically acceptable salts, prodrugs and solvates thereof, are expected to selectively activate μ opioid receptors, and thus, are useful for treating, preventing or ameliorating disorders responsive to the selective activation of μ opioid receptors.

Thus, the present invention provides compounds represented by Formula I:

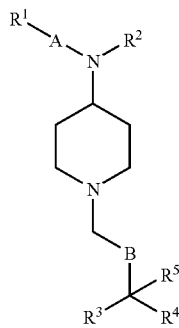

wherein
A is cycloalkyl, heterocycloalkyl, aryl, or heteroaryl;
$R^1$ is:
H or halo; or
$C_{1-6}$alkyl, $C_{2-6}$alkenyl, $C_{2-6}$alkynyl, —O—$C_{1-6}$alkyl, —O—$C_{2-6}$alkenyl, or —O—$C_{2-6}$alkynyl, any of which is optionally substituted; or
—$NR^6R^7$, wherein each of $R^6$ and $R^7$ is independently selected from the group consisting of H, optionally substituted $C_{1-6}$alkyl, optionally substituted $C_{2-6}$alkenyl, and optionally substituted $C_{2-6}$alkynyl;
$R^2$ is $C_{1-6}$alkyl, $C_{2-6}$alkenyl, $C_{2-6}$alkynyl, —C(=O)$C_{1-6}$alkyl, —C(=O)$C_{2-6}$alkenyl, —C(=O)$C_{2-6}$alkynyl, —S(=O)$C_{1-6}$alkyl, —S(=O)$C_{2-6}$alkenyl, —S(=O)$C_{2-6}$alkynyl, $SO_2C_{1-6}$alkyl, $SO_2C_{2-6}$alkenyl, $SO_2C_{2-6}$alkynyl, —$CO_2C_{1-6}$alkyl, —$CO_2C_{2-6}$alkenyl, or —$CO_2C_{2-6}$alkynyl, any of which is optionally substituted;

B is $(CH_2)_m$ wherein m is an integer 0 to 12, and preferably 1, 2 or 3;
$R^3$ and $R^4$ are each independently selected from the group consisting of cycloalkyl, heterocycloalkyl, aryl and heteroaryl;
$R^5$ is H, cyano, $C_{1-6}$ alkyl, $C_{2-6}$ alkenyl, $C_{2-6}$ alkynyl, —C(=O)NH$C_{1-6}$alkyl, —C(=O)N($C_{1-6}$alkyl)$_2$, alkylaminocarbonyl, dialkylaminocarbonyl or cycloaminocarbonyl;
and the pharmaceutically acceptable salts, prodrugs and solvates thereof.

In one embodiment, A is aryl or heteroaryl. In a preferred embodiment, A may be selected from phenyl, pyridinyl, pyrimidinyl, pyrazinyl, pyridzinyl, pyrrolyl, oxazolyl, thienyl, pyridyl, triazolyl, oxadiazolyl, and furanyl. In a preferred embodiment, A is phenyl.

In another embodiment, A is cycloalkyl, and preferably a $C_{5-9}$ cycloalkyl. Examples of such rings include cyclopentyl, cyclohexyl, cycloheptyl, cyclooctyl and cyclononyl.

In another embodiment, $R^1$ is H or halo.
In another embodiment, $R^1$ is $C_{1-6}$alkyl, $C_{2-6}$alkenyl or $C_{2-6}$alkynyl.
In another embodiment, $R^1$ is —$NR^6R^7$.
In another embodiment, $R^2$ is —C(=O)$C_{1-6}$alkyl. Examples of such substituents include carbonylmethyl, carbonylethyl, carbonylpropyl, carbonylbutyl, and carbonylpentyl, carbonylhexyl.

In another embodiment, $R^2$ is —C(=O)$C_{2-6}$alkenyl or —C(=O)$C_{2-6}$alkynyl.

In another embodiment, $R^2$ is —S(=O)$C_{1-6}$alkyl, —S(=O)$C_{2-6}$alkenyl, —S(=O)$C_{2-6}$alkynyl, $SO_2C_{1-6}$alkyl, $SO_2C_{2-6}$alkenyl, or $SO_2C_{2-6}$alkynyl.

In another embodiment, m is 1, 2 or 3.
Useful compounds of the present invention include:
N-(1-(3,3-diphenylpropyl)piperidin-4-yl)-N-phenylpropionamide;
N-(1-(3-cyano-3,3-diphenylpropyl)piperidin-4-yl)-N-phenylpropionamide;
N,N-dimethyl-2,2-diphenyl-4-(4-N-phenylpropionamido) piperidin-1-yl)butanamide;
N-(1-(4-oxo-3,3-diphenyl-4-pyrrolidin-1-yl)butyl)piperidin-4-yl)-N-phenylproionamide;
and the pharmaceutically acceptable salts, prodrugs and solvates thereof.

As used herein, "cycloalkyl" refers to a group selected from $C_3$-$C_{12}$ cycloalkyl, and preferably a $C_{5-9}$ cycloalkyl. Typical cycloalkyl groups include cyclopropyl, cyclobutyl, cyclopentyl, cyclohexyl, cycloheptyl, cyclooctyl, and cyclononyl.

As used herein, "heterocycloalkyl" refers to a group selected from saturated 3-12 membered monocyclic rings, which contain carbon atoms and from one to four heteroatoms independently selected from the group consisting of O, N and/or S. Examples of heterocyclic ring systems include, piperidine, pyrrolidine, piperazine, morpholine, imidazoline, pyrazolidine, benzodiazepines and the like.

As used herein, "aryl" refers to a group selected from $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

As used herein, "heteroaryl" refers to a group having from 5 to 14 ring atoms; 6, 10 or 14 π electrons shared in a cyclic array; and containing carbon atoms and 1, 2 or 3 oxygen, nitrogen and/or sulfur heteroatoms. Examples of heteroaryl groups include thienyl, benzo[b]thienyl, naphtha[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinoolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl.

As used herein, halo or halogen refers to fluoro, chloro, bromo or iodo.

As used herein, a "$C_1$-$C_6$ alkyl" is selected from straight-chained and branched non-cyclic hydrocarbons having from 1 to 6 carbon atoms. Representative straight chain —$C_1$-$C_6$ alkyl groups include -methyl, -ethyl, -n-propyl, -n-butyl, -n-pentyl, and -n-hexyl. Representative branched —$C_1$-$C_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

As used herein, a "$C_2$-$C_6$ alkenyl" is selected from straight chain and branched non-cyclic hydrocarbons having from 2 to 6 carbon atoms and including at least one carbon-carbon double bond. Representative straight chain and branched $C_2$-$C_6$ alkenyl groups include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, 2-hexenyl, and 3-hexenyl.

As used herein, a "$C_2$-$C_6$ alkynyl" is selected from straight chain and branched non-cyclic hydrocarbon having from 2 to 6 carbon atoms and including at least one carbon-carbon triple bond. Representative straight chain and branched $C_2$-$C_6$ alkynyl groups include -acetylenyl, -propynyl, -1-butyryl, -2-butyryl, -1-pentynyl, -2-pentynyl, -3-methyl-1-butynyl, -4-pentynyl, -1-hexynyl, -2-hexynyl, and -5-hexynyl.

As used herein, the term "amino" or "amino group" refers to —$NH_2$.

Useful alkylaminocarbonyl groups include N-methylaminocarbonyl, N-ethylaminocarbonyl, N-propylaminocarbonyl, N-butylaminocarbonyl, N-pentylaminocarbonyl, N-hexylaminocarbonyl and N-octylaminocarbonyl.

Useful dialkylaminocarbonyl groups include N,N-dimethylaminocarbonyl-, N,N-diethylaminocarbonyl, N,N-dipropylaminocarbonyl and N-ethyl-N-methylaminocarbonyl.

Useful cycloaminocarbonyl groups include 1-aziridinylcarbonyl, 1-azetidinylcarbonyl, 1-pyrrolidinylcarbonyl, 1-piperidinylcarbonyl and N-methylpiperiazinylcarbonyl.

As used herein, the term "optionally substituted" refers to a group that is unsubstituted or substituted with one or more substituents. For example, where the groups $C_1$-$C_6$ alkyl, $C_2$-$C_6$ alkenyl, $C_2$-$C_6$ alkynyl, —O—$C_1$-$C_6$ alkyl, —O—$C_2$-$C_6$ alkenyl, and —O—$C_2$-$C_5$ alkynyl are referred to as being optionally substituted, they may or may not be substituted. Where substituted, they may be substituted with a group selected from the group consisting of halo, halo($C_{1-6}$)alkyl, halo$_2$($C_{1-6}$)alkyl, halo$_3$($C_{1-6}$)alkyl, aryl, heteroaryl, cycloalkyl, heterocycloalkyl, $C_{1-6}$alkyl, $C_{2-6}$alkenyl, $C_{2-6}$alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxyl($C_{1-6}$)alkyl, amino($C_{1-6}$)alkyl, carboxy($C_{1-6}$)alkyl, alkoxy($C_{1-6}$)alkyl, nitro, amino, ureido, cyano, alkylcarbonylamino, hydroxyl, thiol, alkylcarbonyloxy, azido, alkoxy, carboxy, aminocarbonyl, and $C_{1-6}$alkylthiol. Preferred optional substituents include halo, halo($C_{1-6}$)alkyl, halo$_2$($C_{1-6}$)alkyl, halo$_3$($C_{1-6}$)alkyl, hydroxyl($C_{1-6}$)alkyl, amino($C_{1-6}$)alkyl, hydroxyl, nitro, $C_{1-6}$alkyl, $C_{1-6}$alkoxy and amino. Preferred numbers of optional substituents are 1, 2 or 3.

The invention disclosed herein also encompasses prodrugs of the disclosed compounds. Prodrugs are considered to be any covalently bonded carriers that release an active compound of Formula I in vivo. Non-limiting examples of prodrugs include esters of compounds of Formula I, and these may be prepared by reacting such compounds with anhydrides such as succinic anhydride.

The invention disclosed herein also encompasses isotopically-labeled (i.e. radio-labeled) compounds of Formula I. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$, respectively, and preferably $^3H$, $^{11}C$, and $^{14}C$. Isotopically-labeled (or radio-labeled) compounds of the present invention can be prepared by methods known in the art. For example, tritiated compounds of Formula I can be prepared by introducing tritium into the particular compound of Formula I, for example, by catalytic dehalogenation with tritium. This method may include reacting a suitably halogen-substituted precursor of a compound of Formula I with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol.* 1, *Labeled Compounds (Part A)*, Chapter 6 (1987). $^{14}C$-labeled compounds can be prepared by employing starting materials having a $^{14}C$ carbon.

The present invention is also directed to the use of radiolabeled compounds of Formula I, as well as their pharmaceutically acceptable salts, prodrugs and solvates, as radioligands for their binding site on an opioid receptor. A radiolabeled compound of Formula I can be used to characterize specific receptor binding of a test or candidate compound. Such radio-labeled compounds binding assays can provide an alternative to animal testing for the evaluation of structure-activity relationships. In a non-limiting embodiment, the present invention provides a method for screening a candidate compound for the ability to bind to an opioid receptor comprising: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Some of the compounds disclosed herein may contain one or more asymmetric centers and may thus give rise to enantiomers, diastereomers, and other stereoisomeric forms. The present invention is meant to encompass all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The invention disclosed herein also encompasses all salts of the disclosed compounds. In one embodiment, the present invention includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicylohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

The invention disclosed herein also encompasses solvates of the disclosed compounds. One type of solvate is a hydrate. Solvates typically do not contribute significantly to the physiological activity or toxicity of the compounds and as such can function as pharmacological equivalents.

Since compounds of Formula I may be useful as opioid receptor agonists, a number of diseases and conditions mediated by opioid receptor activation can be treated by employing these compounds. The present invention thus provides a method of treating, preventing, or ameliorating pain (e.g. chronic pain, neuropathic pain, inflammatory pain, surgical pain or acute pain), or diarrhea in a mammal. In one embodiment, the invention provides a method of treating pain. In one embodiment, the type of pain is chronic pain. In another embodiment, the type of pain is chronic neuropathic pain. In another embodiment, the type of pain is inflammatory pain. In another embodiment, the type of pain is surgical pain. In another embodiment, the type of pain is acute pain. In each instance, such method of treatment, prevention or amelioration requires administering to a mammal in need of such treatment, prevention or amelioration an amount of a compound of the present invention that is therapeutically effective in achieving the desired result (i.e. treatment, prevention or amelioration). In one embodiment, the amount of such compound is that amount effective to activate opioid receptors in vivo.

Chronic pain includes, but is not limited to, inflammatory pain, postoperative pain, cancer pain, osteoarthritis pain, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, *Inflammatory Pain; In: Textbook of Pain*, Wall and Melzack eds., 3$^{rd}$ ed., 1994). Inflammation often occurs at the site of injured tissue, or foreign material, and contributes to the process of tissue repair and healing. The cardinal signs of inflammation include erythema (redness), heat, edema (swelling), pain and loss of function. The majority of patients with inflammatory pain do not experience pain continually, but rather experience enhanced pain when the inflamed site is moved or touched. Inflammatory pain includes, but is not limited to, osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain may also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

Acute pain is any pain which lasts less than 3 consecutive months, and includes but is not limited to the pain experienced as a result of surgery, a minor cut, a sprained ankle, a mild burn, or being struck by an object.

The present invention is also directed more generally to a method for treating a disorder that can be treated by activating opioid receptors, and particularly the selective activation of µ-opioid receptors, in an animal suffering from said disorder, said method comprising administering to the animal an amount of a compound of Formula I, or a pharmaceutically acceptable, salt, prodrug or solvate thereof, that can activate opioid receptors, and more specifically that can activate μ-opioid receptors. A compound of Formula I is considered to be selective for the activation of μ-opioid receptors when the Ki at μ-opioid receptors (as determined by in vitro assays similar to those described below) is lower than the Ki at the δ- and κ-opioid receptors. In one embodiment, compounds of Formula I have a Ki at the δ- and κ-opioid receptors that is at least about 5× higher than at the μ-opioid receptors. In another embodiment, compounds of Formula I have a Ki at the δ- and κ-opioid receptors that is at least about 10× higher than at the μ-opioid receptors. In another embodiment, compounds of Formula I have a Ki at the δ- and κ-opioid receptors that is at least about 100× higher than at the μ-opioid receptors. In another embodiment, compounds of Formula I have a Ki at the δ- and κ-opioid receptors that is at least about 500× higher than at the μ-opioid receptors. In another embodiment, compounds of Formula I have a Ki at the δ- and κ-opioid receptors that is at least about 1,000× higher than at the μ-opioid receptors. In another embodiment, compounds of Formula I have a Ki at the δ- and μ-opioid receptors that is at least about 10,000× higher than at the μ-opioid receptors.

The present invention also provides the use of a compound of Formula I, or a pharmaceutically acceptable salt, prodrug or solvate thereof, in the manufacture of a medicament for treating a disorder that can be treated by activating opioid receptors in an animal suffering from said disorder. In one embodiment, the disorder can be treated by selectively activating μ-opioid receptors. In another embodiment, the disorder is pain or diarrhea.

Synthesis of Compounds

The compounds of the present invention can be prepared using methods known to those skilled in the art in view of this disclosure. For example, compounds of Formula I where A is phenyl, $R^1$ is H, $R^2$ is $MeCH_2CO$, B is $CH_2$, $R^3$ and $R^4$ are each phenyl, and $R^5$ is H, CN, $CONMe_2$, or $CON(CH_2)_4$), can be prepared as shown in Scheme 1.

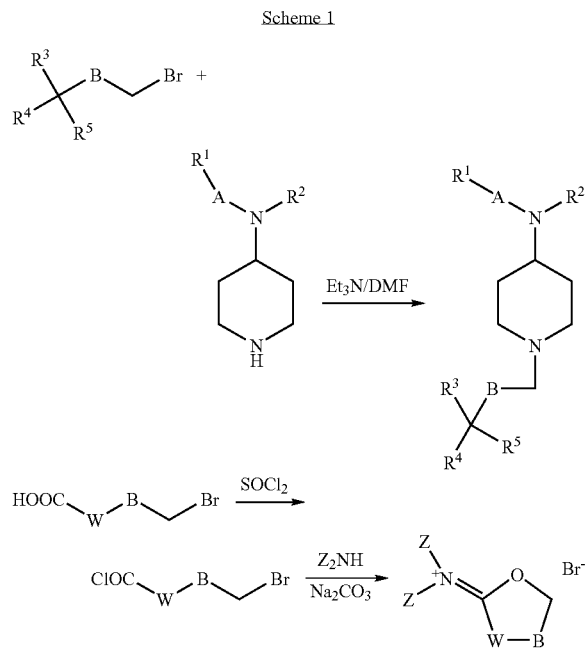

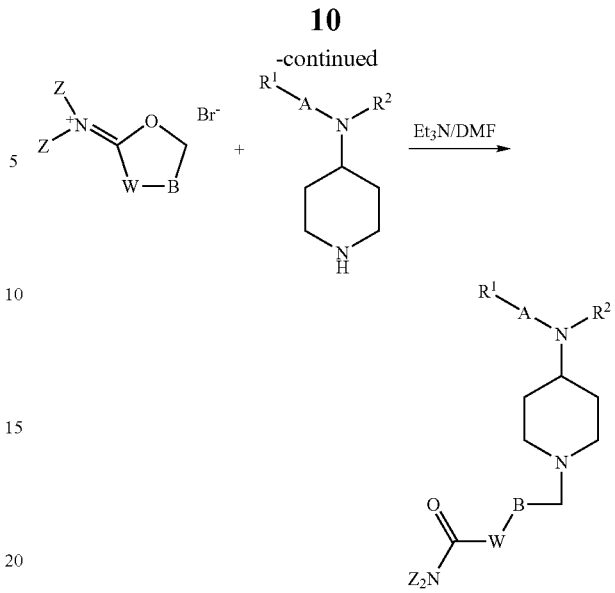

W is $CR^3R^4$ and each Z is a ($C_1$-$C_4$ alkyl) group.

Testing of Compounds

In Vitro μ-Opioid Receptor Binding Assays

μ-opioid Receptor Binding Assay Procedures:
Radioligand dose-displacement binding assays for μ-opioid receptors used 0.2 nM[$^3$H]-diprenorphine (NEN, Boston, Mass.), with 5-20 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 1-2 hr at room temperature. Binding reactions were terminated by rapid filtration onto 96-well Unifilter GF/C filter plates (Packard, Meriden, Conn.) presoaked in 0.5% polyethylemimine using a 96-well tissue harvester (Brandel, Gaithersburg, Md.) followed by performing three filtration washes with 500 μl of ice-cold binding buffer. Filter plates were subsequently dried at 50° C. for 2-3 hours. BetaScint scintillation cocktail (Wallac, Turku, Finland) was added (50 μl/well), and plates were counted using a Packard Top-Count for 1 min/well. The data were analyzed using the one-site competition curve fitting functions in GraphPad PRISM v. 3.0 (San Diego, Calif.), or an in-house function for one-site competition curve-fitting.

μ-opioid Receptor Binding Data:
Generally, the lower the Ki value, the more effective the phenylpropionamide compounds will be at treating pain or diarrhea. Typically, the phenylpropionamide compounds will have a Ki (nM) of about 300 or less for binding to μ-opioid receptors. In one embodiment, the phenylpropionamide compounds will have a Ki (nM) of about 100 or less. In one embodiment, the phenylpropionamide compounds will have a Ki (nM) of about 50 or less. In one embodiment, the phenylpropionamide compounds will have a Ki (nM) of about 20 or less. In another embodiment, the phenylpropionamide compounds of the present invention will have a Ki (nM) of about 10 or less. In still another embodiment, the phenylpropionamide compounds of the present invention will have a Ki (nM) of about 1 or less. In still another embodiment, the phenylpropionamide compounds of the present invention will have a Ki (nM) of about 0.1 or less. N-(1-(4-oxo-3,3-diphenyl-4-(pyrrolidin-1-yl)butyl)piperidin-4-yl)-N-phenylpropionamide, an illustrative phenylpropionamide compound, has a Ki (nM) of 19.17 for binding to µ-opioid receptors.

In Vitro ORL-1 Receptor Binding Assay

ORL-1 Receptor Binding Assay Procedure:
Membranes from recombinant HEK-293 cells expressing the human opioid receptor-like receptor (ORL-1) (Receptor Biology) were prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes were collected by centrifugation at 30,000×g for 15 min at 4° C. and pellets resuspended in hypotonic buffer to a final concentration 1-3 mg/ml. Protein concentrations were determined using the BioRad protein assay reagent with bovine serum albumen as standard. Aliquots of the ORL-1 receptor membranes were stored at −80° C.

Radioligand binding assays (screening and dose-displacement) used 0.1 nM [$^3$H]-nociceptin (NEN; 87.7 Ci/mmole) with 10-20 µg membrane protein in a final volume of 500 µl binding buffer (10 mM $MgCl_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at room temperature. Binding reactions were terminated by rapid filtration onto 96-well Unifilter GF/C filter plates (Packard) presoaked in 0.5% polyethylenimine (Sigma). Harvesting was performed using a 96-well tissue harvester (Packard) followed by three filtration washes with 500 µl ice-cold binding buffer. Filter plates were subsequently dried at 50° C. for 2-3 hours. Fifty µl/well scintillation cocktail (BetaScint; Wallac) was added and plates were counted in a Packard Top-Count for 1 min/well. The data from screening and dose-displacement experiments were analyzed using Microsoft Excel and the curve fitting functions in GraphPad PRISM™, v. 3.0, respectively, or an in-house function for one-site competition curve-fitting.

ORL-1 Receptor Binding Data:
Typically, the phenylpropionamide compounds will have a Ki (nM) of about 300 or less for binding to ORL-1 receptors. In one embodiment, the phenylpropionamide compounds will have a Ki (nM) of about 100 or less. In one embodiment, the phenylpropionamide compounds will have a Ki (nM) of about 50 or less. In one embodiment, the phenylpropionamide compounds will have a Ki (nM) of about 20 or less. In another embodiment, the phenylpropionamide compounds of the present invention will have a Ki (nM) of about 10 or less. In still another embodiment, the phenylpropionamide compounds of the present invention will have a Ki (nM) of about 1 or less. In still another embodiment, the phenylpropionamide compounds of the present invention will have a Ki (nM) of about 0.1 or less.

In Vitro µ-Opioid Receptor Functional Assays

µ-Opioid Receptor Functional Assay Procedures:
[$^{35}$S]GTPγS functional assays were conducted using freshly thawed µ-receptor membranes. Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/ml), saponin (10 mg/ml), GDP (3 mM) and [$^{35}$S]GTPγS (0.20 nM; NEN). The prepared membrane solution (190 µl/well) was transferred to 96-shallow well polypropylene plates containing 10 µl of 20× concentrated stock solutions of the agonist DAMGO prepared in dimethyl sulfoxide (DMSO). Plates were incubated for 30 min at room temperature with shaking. Reactions were terminated by rapid filtration onto 96-well Unifilter GF/B filter plates (Packard, Meriden, Conn.) using a 96-well tissue harvester (Brandel, Gaithersburg, Md.) followed by three filtration washes with 200 µl of ice-cold wash buffer (10 mM $NaH_2PO_4$, 10 mM $Na_2HPO_4$, pH 7.4). Filter plates were subsequently dried at 50° C. for 2-3 hr. BetaScint scintillation cocktail (Wallac, Turku, Finland) was added (50 µl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

µ-Opioid Receptor Functional Data:
µ GTP $EC_{50}$ is the concentration of a compound providing 50% of the maximal response for the compound at a µ-opioid receptor. Phenylpropionamide compounds typically having a µ GTP $EC_{50}$ (nM) of about 5000 or less stimulate µ-opioid receptor function. In one embodiment, the phenylpropionamide compounds of the present invention will have a µ GTP $EC_{50}$ (nM) of about 1000 or less. In one embodiment, the phenylpropionamide compounds of the present invention will have a µ GTP $EC_{50}$ (nM) of about 500 or less. In one embodiment, the phenylpropionamide compounds of the present invention will have a µ GTP $EC_{50}$ (nM) of about 200 or less. In still another embodiment, the phenylpropionamide compounds of the present invention will have a µ GTP $EC_{50}$ (nM) of about 100 or less. In one embodiment, the phenylpropionamide compounds of the present invention will have a µ GTP $EC_{50}$ (nM) of about 60 or less. In still another embodiment, the phenylpropionamide compounds of the present invention will have a µ GTP $EC_{50}$ (nM) of about 10 or less. In still another embodiment, the phenylpropionamide compounds will have a µ GTP $EC_{50}$ (nM) of about 1 or less. In still another embodiment, the phenylpropionamide compounds will have a µ GTP $EC_{50}$ (nM) of about 0.1 or less.

µ GTP Emax % is the maximal effect elicited by a compound relative to the effect elicited by [D-Ala2, N-methyl-Phe4 Gly-ol5]-enkephalin (DAMGO), a standard µ agonist. Generally, the µ GTP Emax (%) value measures the efficacy of a compound to treat or prevent pain or diarrhea. Typically, the phenylpropionamide compounds of the present invention will have a µ GTP Emax (%) of greater than 50%. In one embodiment the phenylpropionamide compounds will have a µ GTP Emax of greater than 75%. In still another embodiment, the phenylpropionamide compounds will have a µ GTP Emax of greater than 88%. In still another embodiment the phenylpropionamide compounds will have a µ GTP Emax of greater than 100%.

In Vitro ORL-1 Receptor Functional Assay

ORL-1 Receptor [35] GTPγS Binding Assay Procedure:
Membranes from recombinant HEK-293 cells expressing the human opioid receptor-like (ORL-1) (Receptor Biology) were prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3 mg/ml. Protein concentrations were determined using the BioRad protein assay reagent with bovine serum albumen as standard. Aliquots of the ORL-1 receptor membranes were stored at −80° C.

Functional binding assays were conducted as follows. ORL-1 membrane solution was prepared by sequentially adding final concentrations of 0.066 μg/μl ORL-1 membrane protein, 10 μg/ml saponin, 3 μM GDP and 0.20 nM [35S] GTPγS to binding buffer (100 mM NaCl, 10 mM $MgCl_2$, 20 mM HEPES, pH 7.4) on ice. The prepared membrane solution (190 μl/well) was transferred to 96-shallow well polypropylene plates containing 10 μl of 20× concentrated stock solutions of agonist/nociceptin prepared in DMSO. Plates were incubated for 30 min at room temperature with shaking. Reactions were terminated by rapid filtration onto 96-well Unifilter GF/B filter plates (Packard) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates were subsequently dried at 50° C. for 2-3 hours. Fifty μl/well scintillation cocktail (BetaScint; Wallac) was added and plates were counted in Packard Top-Count for 1 min/well. Data are analyzed using the sigmoidal dose-response curve fitting functions in Graph-Pad PRISM v. 3.0, or an in-house function for non-linear, sigmoidal dose-response curve-fitting.

ORL-1 Receptor Functional Data:

ORL-1 GTP $EC_{50}$ is the concentration of a compound providing 50% of the maximal response for the compound at an ORL-1 receptor. Phenylpropionamide compounds typically having an ORL-1 GTP $EC_{50}$ (nM) of about 5000 or less stimulate ORL-1 receptor function. In one embodiment, the phenylpropionamide compounds of the present invention will have an ORL-1 GTP $EC_{50}$ (nM) of about 1000 or less. In still another embodiment, the phenylpropionamide compounds of the present invention will have an ORL-1 GTP $EC_{50}$ (nM) of about 100 or less. In still another embodiment, the phenylpropionamide compounds of the present invention will have an ORL-1 GTP $EC_{50}$ (nM) of about 10 or less. In still another embodiment, the phenylpropionamide compounds will have an ORL-1 GTP $EC_{50}$ (nM) of about 1 or less. In still another embodiment, the phenylpropionamide compounds will have an ORL-1 GTP $EC_{50}$ (nM) of about 0.1 or less.

ORL-1 GTP Emax % is the maximal effect elicited by a compound relative to the effect elicited by nociceptin, a standard ORL-1 agonist. Typically, the phenylpropionamide compounds of the present invention will have an ORL-1 GTP Emax (%) of greater than 50%. In one embodiment the phenylpropionamide compounds will have an ORL-1 GTP Emax of greater than 75%. In still another embodiment, the phenylpropionamide compounds will have an ORL-1 GTP Emax of greater than 88%. In still another embodiment the phenylpropionamide compounds will have an ORL-1 GTP Emax of greater than 100%.

In Vivo Pharmacology

The compounds of the present invention can be tested for their anti-nociceptive activity in the formalin model, which has been described in Hunskaar, S., O. B. Fasmer, and K. Hole, *J Neurosci Methods* 14: 69-76 (1985). Male Swiss Webster NIH mice (20-30 g; Harlan, San Diego, Calif.) can be used in all experiments. Food is withdrawn on the day of the experiment. Mice are placed in plexiglass jars for at least 1 hour to acclimate to the environment. Following the acclimation period mice are weighed and given either the compound of interest administered i.p. or p.o., or the appropriate volume of vehicle (10% Tween-80) as control. Fifteen minutes after the i.p. dosing, and 30 minutes after the p.o. dosing, mice are injected with formalin (20 μl of 5% formaldehyde solution in saline) into the dorsal surface of the right hind paw. Mice are transferred to plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as the licking/biting between 0-5 minutes, and the late phase is measured from 15-50 minutes after formalin injection. Differences between vehicle and drug treated groups can be analyzed by one-way analysis of variance (ANOVA). A p value<0.05 is considered significant. Compounds are considered to be efficacious for treating acute and chronic pain if they have activity in blocking both the early and second phase of formalin-induced paw-licking activity.

Compounds can be tested for their potential to treat chronic pain (i.e. anti-allodynic and anti-hyperalgesic activities) using the Chung model of peripheral neuropathy (Kim and Chung, *Pain* 50: 355-363 (1992)). Male Sprague-Dawley rats weighing between 200-225 g are anesthetized with halothane (1-3% in a mixture of 70% air and 30% oxygen), and their body temperature controlled during anesthesia through use of a homeothermic blanket. A 2 cm dorsal midline incision is then made at the L5 and L6 spinal nerves, and the paravertebral muscle groups retracted bilaterally. L5 and L6 spinal nerves are then exposed, isolated, and tightly ligated with δ-0 or 7-0 silk suture. A sham operation is performed exposing the contralateral L5 and L6 spinal nerves, without ligating, as a negative control.

Tactile Allodynia:

Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 g (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 g filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to a mammal, e.g. a human, orally at a dose of from abut 0.0025 to about 1500 mg per kg body weight of the mammal, or an equivalent amount of a pharmaceutically acceptable salt, prodrug or solvate thereof, per day to treat, prevent or ameliorate the particular disorder. A useful oral dose of a compound of the present invention administered to a mammal is from about 0.025 to about 50 mg per kg body weight of the mammal, or an equivalent amount of the pharmaceutically acceptable salt, prodrug or solvate thereof. For intramuscular injection, the dose is typically about one-half of the oral dose.

A unit oral dose may comprise from about 0.01 to about 50 mg, and preferably about 0.1 to about 10 mg, of a compound. The unit dose can be administered one or more times daily, e.g. as one or more tablets or capsules, each containing from about 0.01 mg to about 50 mg of the compound, or an equivalent amount of a pharmaceutically acceptable salt, prodrug or solvate thereof.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

In one embodiment, a pharmaceutical composition of the present invention can be administered orally and is formulated into tablets, dragees, capsules or an oral liquid preparation. In one embodiment, the oral formulation comprises extruded multiparticulates comprising the compound of the invention.

In another embodiment, a pharmaceutical composition of the present invention is formulated to be administered rectally, i.e., as suppositories.

In another embodiment, a pharmaceutical composition of the present invention is formulated to be administered by injection.

In another embodiment, a pharmaceutical composition of the present invention is formulated to be administered transdermally, e.g., in a patch formulation.

In another embodiment, a pharmaceutical composition of the present invention is formulated to be administered by inhalation or by intranasal or transmucosal administration.

In another embodiment, a pharmaceutical composition of the present invention is formulated to be administered by the intravaginal route.

A pharmaceutical composition of the present invention can contain from about 0.01 to 99 percent by weight, and preferably from about 0.25 to 75 percent by weight, of active compound(s).

A pharmaceutical composition of the present invention is preferably manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

In one embodiment, pharmaceutical compositions of the invention are prepared by incorporating compounds of Formula I into a controlled release formulation, whereby a steady state plasma level of a compound of Formula I can be maintained.

One manner in which these steady state plasma levels can be obtained is by using appropriate technologies, e.g., controlled-release formulations, selected to provide an appropriate release profile. The appropriate release profile can be achieved for example, using single or multiparticulate delivery systems. Examples of single delivery systems include, but are not limited to, wax matrix tablets, hydrophilic matrix tablets and tablets with controlled-release coatings. Examples of multiparticulate systems include, but are not limited to, matrix systems such as melt extruded multiparticulates (MEMs), or systems based on controlled release coatings such as coated-beads.

In one embodiment, the pharmaceutical compositions of the present invention provide a therapeutic steady state plasma level of a compound of Formula I for a duration of from about 12 h to about 24 h following oral administration. In another embodiment, the pharmaceutical compositions of the present invention provide a therapeutic steady state plasma level of a compound of Formula I for a duration of from about 6 h to about 12 following oral administration.

A method of the present invention, such as a method for treating, preventing, or ameliorating a disorder that can be treated, prevented or ameliorated by activating opioid receptors in an animal in need thereof, can further comprise administering a second therapeutic agent to the animal in combination with a compound of the present invention. In one embodiment, the other therapeutic agent is administered in an effective amount.

Effective amounts of the other therapeutic agents will be known to those skilled in the art depending on the identity of the other therapeutic agent. However, it is within the skilled artisan's purview to determine the other therapeutic agent's optimal effective-amount range.

A compound of the present invention (i.e. the first therapeutic agent) and second therapeutic agent can act additively, or, in one embodiment synergistically. In one embodiment, a compound of the present invention is administered concurrently with a second therapeutic agent; for example, a single composition comprising both an effective amount of a compound of Formula I, and an effective amount of the second therapeutic agent can be administered. Accordingly, the present invention further provides a pharmaceutical composition comprising a combination of a compound of the present invention, the second therapeutic agent, and a pharmaceutically acceptable carrier. Alternatively, a first pharmaceutical composition comprising an effective amount of a compound of Formula I and a second pharmaceutical composition comprising an effect amount of the second therapeutic agent can be concurrently administered. In another embodiment, an effective amount of a compound of the present invention is administered prior or subsequent to administration of an effective amount of the second therapeutic agent. In this embodiment, the compound of the present invention is administered while the second therapeutic agent exerts its therapeutic effect, or the second therapeutic agent is administered while the compound of the present invention exerts its therapeutic effect for treating, preventing or ameliorating a disorder or condition.

The second therapeutic agent can be an opioid agonist, a non-opioid analgesic, an non-steroidal anti-inflammatory agent, an antimigraine agent, an anti-emetic agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, an agent for treating depression, or an agent for treating diarrhea, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tohnetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, Analgesic Antipyretic and Antiinflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996) and Glen R. Hanson, Analgesic, Antipyretic and Anti Inflammatory Drugs in Remington: The Science and Practice of Pharmacy Vol II 1196-1221 (A. R. Gennaro ed. 19th ed. 1995) which are hereby incorporated by reference in their entireties. Suitable Cox-II inhibitors and δ-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating or preventing an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing ALS include, but are not limited to, baclofen, neurotrophic factors, riluzole, tizanidine, benzodiazepines such as clonazepam and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and sertraline; monoamine oxidase inhibitors such as isocarboxazid, pargyline, phenelzine, and tranylcypromine; and psychostimulants such as dextroamphetamine and methylphenidate.

Examples of useful anti-diarrheal agents include, but are not limited to, loperamide, diphenoxylate with atropine, clinidine, octreotide, and cholestyramine.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

N-(1-(3-cyano-3,3-diphenylpropyl)piperidin-4-yl)-N-phenylpropionamide

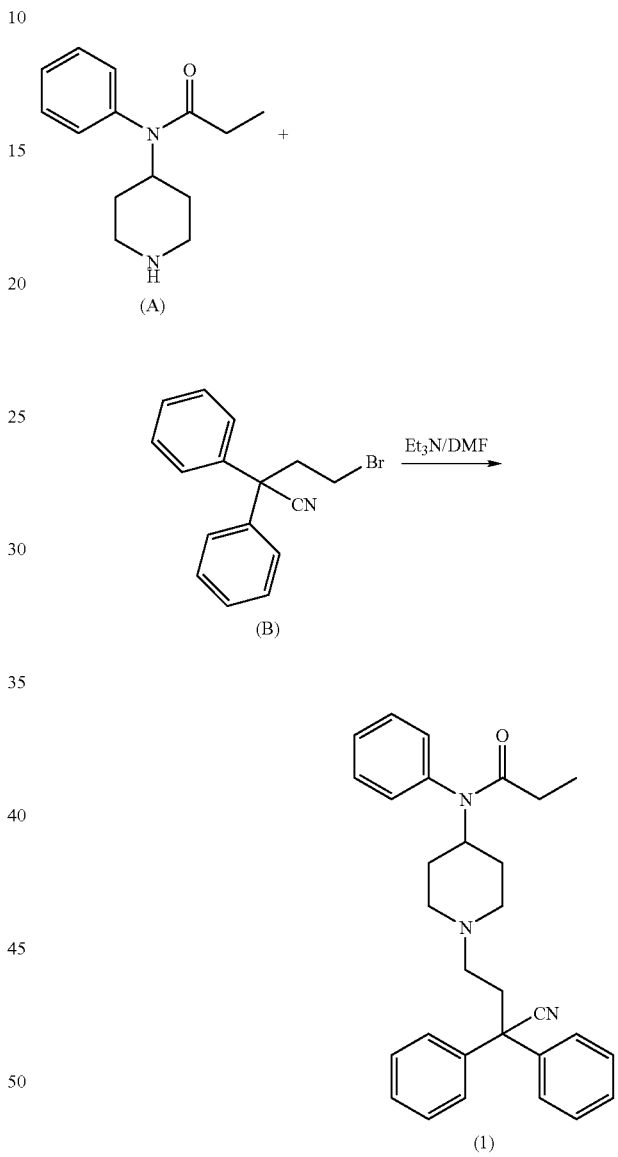

To a solution of (A) (Acros Organics USA) (0.5 mmol) and (B) (Acros Organics USA) (0.5 mmol) in MeCN (1.5 mL) was added triethylamine (2.87 mmol) at the room temperature. Then the mixture was stirred at 60° C. overnight. Direct flash chromatography (70% Hexane/30% EtOAc/3% Et$_3$N) afforded the desired product as a white solid in 75% yield.

Compound (1): purity (HPLC)>97%; MS: m/z 452.1 (M+1); $^1$H NMR (CDCl$_3$): δ 7.40-7.24 (m, 13H), 7.06 (m, 2H), 4.62 (m, 1H), 2.86 (m, 2H), 2.52 (m, 2H), 2.38 (m, 2H), 2.08 (dt, 2H, J=2.0, 11.9 Hz), 1.91 (q, 2H, J=7.5, 14.9 Hz), 1.75 (m, 2H), 1.33 (dq, 2H, J=3.7, 12.3 Hz), 1.00 (t, 3H, J=7.6 Hz) ppm

Example 2

N-(1-3,3-diphenylpropyl)piperidin-4-yl)-N-phenyl-propionamide

Example 3

N,N-dimethyl-2,2-diphenyl-4-(4-(N-phenylpropiona-mido)piperidin-1-yl)butanamide

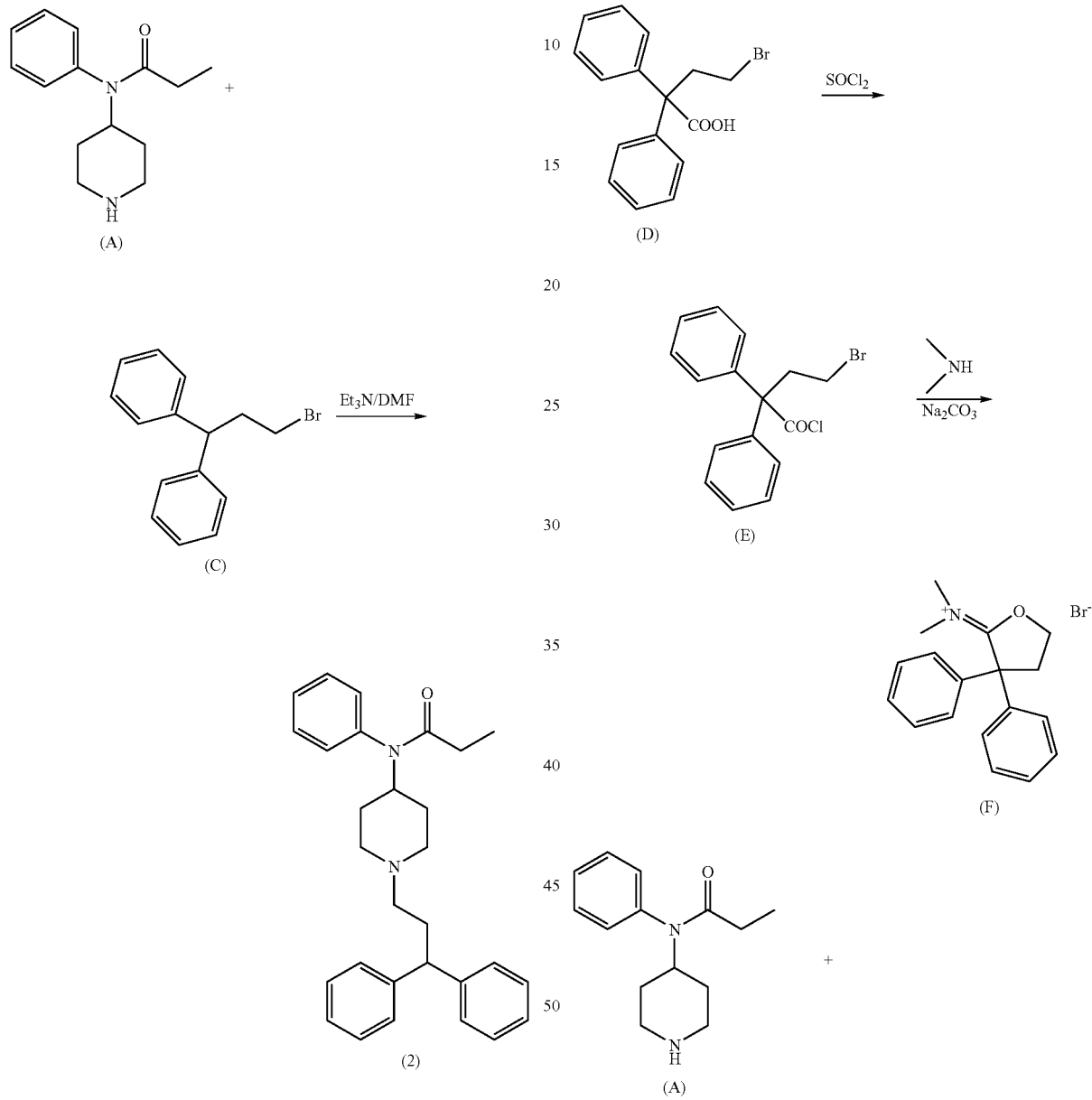

To a solution of (A) (0.5 mmol) and (C) (Acros Organics USA) (0.5 mmol) in MeCN (1.5 mL) was added triethylamine (2.87 mmol) at the room temperature. Then the mixture was stirred at 60° C. overnight. Direct flash chromatography (70% Hexane/30% EtOAc/3% Et$_3$N) afforded the desired product as a white solid in 75% yield.

Compound (2): purity (HPLC)>97%; MS: m/z 427.1 (M+1); $^1$H NMR (CDCl$_3$): δ 7.37 (m, 3H), 7:25-7.12 (m, 10H), 7.06 (m, 2H), 4.62 (m, 1H), 3.88 (t, 1H, J=7.3 Hz), 2.87 (d, 2H, J=11.3 Hz), 2.19 (m, 4H), 2.02 (dt, 2H, J=2.0, 12.1 Hz), 1.91 (q, 2H, J=7.4, 14.9 Hz), 1.74 (m, 2H), 1.37 (dq, 2H, J=4.0, 12.1 Hz), 1.00 (t, 3H, J=7.4 Hz) ppm

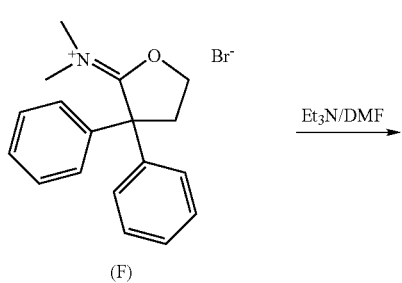

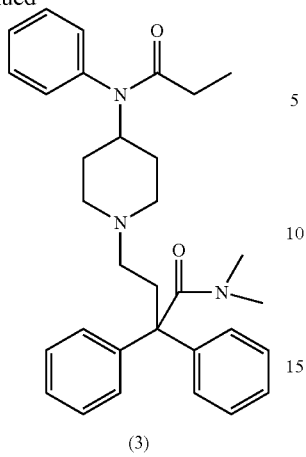

(3)

4-Bromo-2,2-diphenylbutyric acid (D) (Aldrich Chemical Company, Inc.) (23 g, 72 mmol) was suspended in chloroform (150 mL), and thionyl chloride (20 mL) was added dropwise. After addition of thionyl chloride, DMF (0.2 mL) was added, and the resulting solution was heated at reflux for 4 hours. The reaction mixture was then concentrated under reduced pressure to provide 4-bromo-2,2-diphenylbutyric acid chloride (E) as a pale yellow oil that was used for next step without further purification.

To a solution of dimethylamine (2M in THF, 50 mL) and saturated aqueous $Na_2CO_3$ (100 mL) was added dropwise a solution of compound (E) in toluene (100 mL), prepared as described above, at 0° C. The resulting mixture was allowed to stir for 12 hours. The mixture was extracted with toluene (1×30 mL) and chloroform (3×100 mL). The combined extracts were washed with water (1×30 mL), dried over $K_2CO_3$. After evaporation to dryness and crystallization with methyl isobutyl ketone, the desired product (F) dimethyl(tetrahydro-3,3-diphenyl-2-furylidene)ammonium bromide was obtained in 53% yield.

To a solution of (A) (0.5 mmol) and (F) (0.5 mmol) in MeCN (1.5 mL) was added triethylamine (2.87 mmol) at the room temperature. Then the mixture was stirred at 60° C. overnight. Direct flash chromatography (70% Hexane/30% EtOAc/3% $Et_3N$) afforded the desired product as a white solid in 75% yield.

Compound (3): purity (HPLC)>97%; MS: m/z 498.1 (M+1); $^1H$ NMR ($CDCl_3$): δ 7.38-7.22 (m, 13H), 7.06 (m, 2H), 4.56 (m, 1H), 2.96 (m, 2H), 2.78 (m, 2H), 2.32 (m, 4H), 1.96 (m, 5H), 1.88 (q, 2H, J=7.5, 14.8 Hz), 1.64 (s, 3H), 1.29 (dq, 2H, J=3.3, 7.2 Hz), 0.98 (t, 3H, J=7.4 Hz) ppm Example 4

N-(1-(4-oxo-3,3-diphenyl-4-(pyrrolidin-1-yl)butyl)piperidin-4-yl)-N-phenylpropionamide

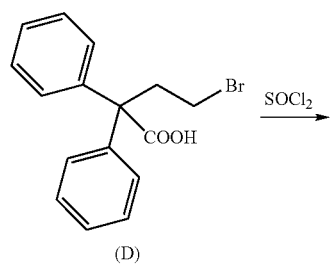

(D)

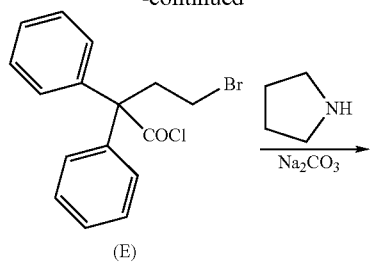

(E)

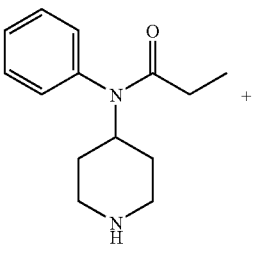

(A)

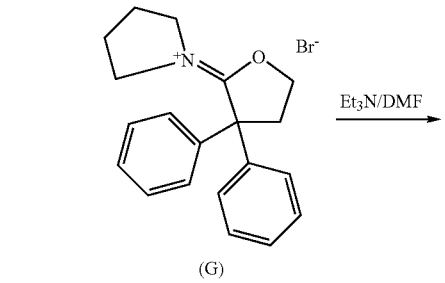

(G)

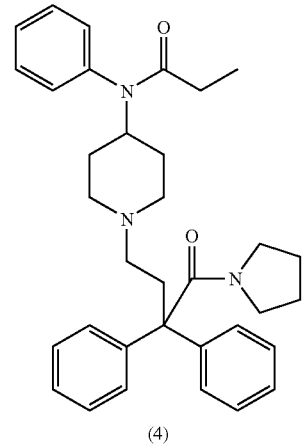 [SMILES: CCC(=O)N(c1ccccc1)C1CCN(CCC(C(=O)N2CCCC2)(c2ccccc2)c2ccccc2)CC1]

(4)

Compound (G) 1-(3,3-diphenyl-dihydrofuran-2-ylidene)-pyrrolidinium bromide was prepared with pyrrolidine following the same procedure as the synthesis of compound (F) dimethyl(tetrahydro-3,3-diphenyl-2-furylidene)ammonium bromide.

To a solution of (A) (0.5 mmol) and (G) (0.5 mmol) in MeCN (1.5 mL) was added triethylamine (2.87 mmol) at room temperature. Then the mixture was stirred at 60° C. overnight. Direct flash chromatography (70% Hexane/30% EtOAc/3% Et$_3$N) afforded the desired product as a white solid in 75% yield.

Compound (4): purity (HPLC)>97%; MS: m/z 524.1 (M+1); $^1$H NMR (CDCl$_3$): δ 7.37-7.22 (m, 13H), 7.06 (m, 2H), 4.56 (m, 1H), 3.56 (t, 2H, J=7.0 Hz), 2.80 (br d, 2H, J=11.8 Hz), 2.44 (t, 2H, J=6.4 Hz), 2.37 (m, 2H), 2.00 (m, 4H), 1.88 (q, 2H, J=7.4, 14.8 Hz), 1.66 (m, 4H), 1.50 (m, 2H), 1.29 (dq, 2H, J=3.9, 12.3 Hz), 0.98 (t, 3H, J=7.2 Hz) ppm Example 5

Compounds of the present invention were tested for μ-opioid receptor binding, and function. TABLE 1 contains binding and functional data for several compounds.

TABLE 1

| Compound | Ki (nM) | GTP EC50 (nM) | GTP Emax (%) |
| --- | --- | --- | --- |
| N-(1-(3-cyano-3,3-diphenylpropyl)piperidin-4-yl)-N-phenylpropionamide | 82.83 | 491.3 | 79.7 |
| N-(1-3,3-diphenylpropyl)piperidin-4-yl)-N-phenylpropionamide | 330.6 | 1005.7 | 56.3 |
| N,N-dimethyl-2,2-diphenyl-4-(4-(N-phenylpropionamido)piperidin-1-yl)butanamide | 36.1 | 143 | 100.3 |
| N-(1-(4-oxo-3,3-diphenyl-4-(pyrrolidin-1-yl)butyl)piperidin-4-yl)-N-phenylpropionamide | 19.17 | 50.6 | 95.8 |

Example 6

Compounds of the present invention were tested for ORL-1 receptor binding, and function. TABLE 2 contains binding and functional data for the same compounds presented in Table 1. The term "ND" means "not determined".

TABLE 2

| Compound | Ki (nM) | GTP EC50 (nM) | GTP Emax (%) |
| --- | --- | --- | --- |
| N-(1-(3-cyano-3,3-diphenylpropyl)piperidin-4-yl)-N-phenylpropionamide | >20 μM | ND | ND |
| N-(1-3,3-diphenylpropyl)piperidin-4-yl)-N-phenylpropionamide | 4398.57 | ND | ND |
| N,N-dimethyl-2,2-diphenyl-4-(4-(N-phenylpropionamido)piperidin-1-yl)butanamide | >20 μM | ND | ND |
| N-(1-(4-oxo-3,3-diphenyl-4-(pyrrolidin-1-yl)butyl)piperidin-4-yl)-N-phenylpropionamide | >20 μM | ND | ND |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

The invention claimed is:
1. A compound of Formula I:

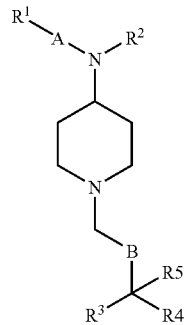

wherein
A is cycloalkyl or phenyl;
$R^1$ is:
H or halo; or
$C_{1-6}$alkyl, $C_{2-6}$alkenyl, $C_{2-6}$alkynyl, —O—$C_{1-6}$alkyl, —O—$C_{2-6}$alkenyl, or —O—$C_{2-6}$alkynyl, any of which is optionally substituted
—NR$^6$R$^7$, wherein each of R$^6$ and R$^7$ is independently selected from the group consisting of H, or $C_{1-6}$alkyl, $C_{2-6}$alkenyl, and $C_{2-6}$alkynyl; any of which is optionally substituted,
$R^2$ is $C_{1-6}$alkyl, $C_{2-6}$alkenyl, $C_{2-6}$alkynyl, —C(=O)$C_{1-6}$alkyl, —C(=O)$C_{2-6}$alkenyl, —C(=O)$C_{2-6}$alkynyl, —S(=O)$C_{1-6}$alkyl, —S(=O)$C_{2-6}$alkenyl, —S(=O)$C_{2-6}$alkynyl, SO$_2$C$_{1-6}$alkyl, SO$_2$C$_{2-6}$alkenyl, SO$_2$C$_{2-6}$alkynyl, —CO$_2$C$_{1-6}$alkyl, —CO$_2$C$_{2-6}$alkenyl, or —CO$_2$C$_{2-6}$alkynyl, any of which is optionally substituted;
wherein optionally substituted means that the group is optionally substituted with one or more substituents independently selected from the group consisting of halo, halo($C_{1-6}$)alkyl, halo$_2$($C_{1-6}$)alkyl, halo$_3$($C_{1-6}$)alkyl, aryl, heteroaryl, cycloalkyl, heterocycloalkyl, $C_{1-6}$alkyl, $C_{2-6}$alkenyl, $C_{2-6}$alkynyl, aryl($C_{1-6}$)alkyl-, aryl($C_{2-6}$)alkenyl-, aryl($C_{2-6}$)alkynyl-, cycloalkyl($C_{1-6}$)alkyl-, heterocyclo($C_{1-6}$)alkyl-, hydroxyl($C_{1-6}$)alkyl-, amino($C_{1-6}$)alkyl-, carboxy($C_{1-6}$)alkyl-, alkoxy($C_{1-6}$)alkyl-, nitro, amino, ureido, cyano, alkylcarbonylamino, hydroxyl, thiol, alkylcarbonyloxy, azido, alkoxy, carboxy, aminocarbonyl, and $C_{1-6}$alkylthiol; and wherein aryl is selected from the group consisting of phenyl, naphthyl, phenanthryl, anthracyl, indenyl, azulenyl, biphenyl, biphenylenyl and fluorenyl;
B is (CH$_2$)$_m$ wherein m is an integer 0 to 12;
R$^3$ and R$^4$ are each phenyl;
R$^5$ is H, —$C_{1-6}$alkyl, $C_{2-6}$alkenyl, $C_{2-6}$alkynyl, —C(=O)NHC$_{1-6}$alkyl, —C(=O)N(C$_{1-6}$alkyl)$_2$, alkylaminocarbonyl, dialkylaminocarbonyl or cycloaminocarbonyl;
and the pharmaceutically acceptable salts thereof.

2. A compound of claim 1 wherein A is phenyl.
3. A compound of claim 1, wherein A is cycloalkyl.
4. A compound of claim 1, wherein R$^1$ is H or halo.
5. A compound of claim 1, wherein R$^1$ is $C_{1-6}$alkyl, $C_{2-6}$alkenyl or $C_{2-6}$alkynyl.
6. A compound of claim 1, wherein R$^1$ is —NR$^6$R$^7$.
7. A compound of claim 1, wherein R$^2$ is C(=O)$C_{1-6}$alkyl.
8. A compound of claim 7, wherein R$^2$ is C(=O)CH$_2$CH$_3$.

9. A compound of claim 1, wherein $R^2$ is —C(=O)$C_{2-6}$alkenyl or —C(=O)$C_{2-6}$alkynyl.

10. A compound of claim 1, wherein m is 1, 2 or 3.

11. The compound of claim 1, wherein said compound is selected from the group consisting of:

N-(1-(3,3-diphenylpropyl)piperidin-4-yl)-N-phenylpropionamide;

N,N-dimethyl-2,2-diphenyl-4-(4-N-phenylpropionamido)piperidin-1-yl)butanamide;

N-(1-(4-oxo-3,3-diphenyl-4-(pyrrolidin-1-yl)butyl)piperidin-4-yl)-N-phenylpropionamide;

and the pharmaceutically acceptable salts thereof.

12. A pharmaceutical composition comprising a compound of claim 1 and at least one pharmaceutically acceptable excipient.

13. The compound of claim 1, wherein $R^2$ is optionally substituted with 1, 2, or 3 substituents.

14. The compound of claim 1, wherein $R^2$ is optionally substituted with one or more substituents independently selected from the group consisting of halo, halo($C_{1-6}$)alkyl, halo$_2$($C_{1-6}$)alkyl, halo$_3$($C_{1-6}$)alkyl, hydroxy($C_{1-6}$)alkyl, amino($C_{1-6}$)alkyl, hydroxyl, nitro, $C_{1-6}$alkyl, $C_{1-6}$alkoxy and amino.

\* \* \* \* \*